United States Patent

Morgan et al.

[11] Patent Number: 5,872,207
[45] Date of Patent: Feb. 16, 1999

[54] N-TERMINAL-MARKED PEPTIDES IMMOBILIZED ON GLASS BEADS AND METHOD OF PREPARATION AND METHOD OF USE THEREOF

[75] Inventors: Barry Arnold Morgan, Franklin, Mass.; Mark Alan Ator, Paoli; James Arthur Gainor, Collegeville, both of Pa.; Thomas Douglas Gordon, Medway, Mass.; Lawrence Ivan Kruse, Haddonfield, N.J.; Teruna Jaya Siahaan, Lawrence, Kans.

[73] Assignee: Sanofi Pharmaceuticals, Inc., New York, N.Y.

[21] Appl. No.: 520,455

[22] Filed: Aug. 29, 1995

Related U.S. Application Data

[63] Continuation-in-part of Ser. No. 941,281, Sep. 4, 1992, abandoned.

[51] Int. Cl.[6] ................................................... C07K 7/00
[52] U.S. Cl. .......................... 530/300; 530/334; 530/345; 530/811; 514/16; 514/17; 435/7.92
[58] Field of Search ................................. 530/334, 811, 530/345; 514/16, 17; 330/816; 435/7.92

[56] References Cited

U.S. PATENT DOCUMENTS

| | | | |
|---|---|---|---|
| 4,066,405 | 1/1978 | Henkin | 23/230 B |
| 4,284,553 | 8/1981 | Brown | 260/112 R |
| 4,368,047 | 1/1983 | Andrade | 435/4 |
| 4,992,383 | 2/1991 | Farnsworth | 436/89 |
| 5,648,462 | 7/1997 | Funakoshi | 530/344 |

OTHER PUBLICATIONS

Tesser, Tetrahedron 32, 1069,1976.
Robinson, Biochimica et Biophys. Acta 242, 659, 1971.
Power S, Meth. Pept. Prot. Seq. Anal. 89–102, 1980.
Wachter Febs Letters 35, 97–102, 1973.

*Primary Examiner*—David Lukton
*Attorney, Agent, or Firm*—Mary P. Bauman; Michael D. Alexander

[57] ABSTRACT

Peptides or peptides having an amino acid-like moiety in place of an amino acid moiety thereof immobilized on glass beads, especially controlled-pore glass beads, by a C-terminal α-carboxyl-ω-amino linker and α-silyl-ω-amino anchor, especially wherein the anchor has the structural formula $$-NH(CH_2)_nSi(OR)_2O-$$

wherein n is 3 and R is hydrogen or the glass bead and the linker has the structural formula $$-[NH(CH_2)_rCO]_s-$$

wherein r is 5 and s is an integer from 1 through 10 and marked by an N-terminal fluorescent marker, especially wherein the N-terminal fluorescent marker is 3-(7-hydroxy-4-coumarinyl)propionyl, and method of preparation thereof and method of use thereof in carrying out biochemical assays, especially wherein the immobilized peptide or peptide having an amino acid-like moiety in place of an amino acid moiety thereof is cleaved by a protease and the resulting fluorescence in the supernatant solution is measured to determine the extent of cleavage, are disclosed.

3 Claims, No Drawings

N-TERMINAL-MARKED PEPTIDES IMMOBILIZED ON GLASS BEADS AND METHOD OF PREPARATION AND METHOD OF USE THEREOF

This application is a continuation-in-part of application Ser. No. 07/941,281, filed on Sep. 4, 1992.

BACKGROUND OF THE INVENTION

1. Field of the Invention

The invention relates to peptides immobilized on glass beads and having N-terminal markers and method of preparation thereof and method of use thereof in carrying out biochemical assays.

2. Information Disclosure Statement

Albericio et al. (Peptides, Walter de Gruyter & Co., Berlin—N.Y., pp. 167–170, 1986) and Büttner et al. (Proceedings of Tenth American Peptide Symposium, pp. 210–211, 1987) describe peptides linked to controlled-pore glass.

Fodor et al. (Science, vol. 251, pp. 767–773, 15 Feb. 1991), which is entitled "Light-Directed, Spatially Addressable Parallel Chemical Synthesis", describes peptides bonded at the carboxy terminals through "[a]mino groups at the ends of linkers" to glass plates and having photoremovable protecting groups or fluorescent labels at the amino terminals. Aminopropyl is specifically described as a linker. Nitrovcratryloxycarbonyl is specifically described as a photoremovable protecting group. Fluorescein isothiocyanate is specifically described as a fluorescent labeling agent. The peptides are described as synthesized by solid phase methods. Two pentapeptides, YGGFL and PGGFL, are described as having been prepared in a checkerboard pattern on a glass plate by stepwise synthesis of the common tetrapeptide followed by selective removal of the photoremovable protecting group using a checkerboard mask followed by addition of Y (tyrosyl) to form YGGFL followed by selective removal of the photoremovable protecting group from the areas of the plate where it was masked in the first removal followed by addition of P (prolyl) to form PGGFL. Selective detection of YGGFL by mouse monoclonal antibody 3E7, which does not bind PGGFL, followed by fluorescein-labeled goat antibody to mouse monoclonal antibody 3E7 followed by scanning of the plate with an epifluorescence microscope whereby the squares occupied by YGGFL showed fluorescence is described. By similar technique fluorescent antibody analysis of a 32×32 checkerboard array of 1024 peptides ranging in length from 0 to 10 amino acids and each occupying a 400 $\mu$m-square area of the plate is also described.

Lam et al. (Nature, vol. 354, pp. 82–84, 7 Nov. 1991) describes peptides linked to resin beads wherein each bead contains a single peptide. Using all of the natural amino acids except cysteine (19), 19 separate reaction vessels and stepwise synthesis beads containing all of the possible pentapeptides thereof ($19^5$=2,467,099) were prepared as a mixture, which is referred to as "the peptide-bead library" and which was allowed to react with solutions of acceptor molecules coupled to an enzyme (alkaline phosphatase) or fluorescein. In tests using a monoclonal antibody against $\beta$-endorphin and streptavidin as acceptor molecules only a few beads became intensely stained (6 and 23 respectively) and these could be separated manually from the beads which were not intensely stained. The acceptor molecules were removed from the beads and each bead, which contained 50–200 picomole of peptide, was analyzed for the amino acid sequence of its linked pentapeptide using an automated peptide microsequencer. As an anti-$\beta$-endorphin ligand the synthetic pentapeptide YGGFQ (Q represents glutaminyl) having a $K_i$ value of 15.0±1.7 nM (the natural pentapeptide YGGFL has a $K_i$ value of 17.5±3.2 nM) was thus identified. As binders of streptavidin 19 of 23 pentapeptides were identified as having the HPQ sequence of amino acids and the remaining 4 of 23 pentapeptides were identified as having the HPM sequence of amino acids.

The Albericio et al. and Büttner et al. references relate only to solid phase synthesis of peptides and do not describe or suggest peptides immobilized on a solid support and designed as tools for biochemical assay. The method of the Fodor et al. reference is limited to assays that can be carried out on the solid surface of a glass plate. The method of the Lam et al. reference depends on interaction of a fluorescent acceptor molecule with a peptide immobilized on a single glass bead and on finding and removing the resulting single fluorescent glass bead from many others in order to determine the immobilized peptide thereof. Neither the Fodor et al. reference nor the Lam et al. reference relates to cleavage of an immobilized peptide or to use of a supernatant solution for biochemical assay. The presently described and claimed invention relates to a peptide immobilized on a glass bead, which is in practice one of many glass beads each having the same immobilized peptide, for use as a substrate for a protease, cleavage by which results in a fluorescent peptide fragment in the supernatant solution and a peptide fragment on the glass bead, either or both of which can be analyzed to determine the extent and site of cleavage and is thus distinguished from the cited references.

SUMMARY OF THE INVENTION

In a composition of matter aspect the invention is a peptide or a peptide having an amino acid-like moiety in place of an amino acid moiety thereof immobilized on a glass bead by a C-terminal $\alpha$-carboxyl-$\omega$-amino linker and $\alpha$-silyl-$\omega$-amino anchor and marked by an N-terminal fluorescent marker.

In a first process aspect the invention is the process of preparing the composition of matter aspect of the invention which comprises reacting a glass bead having an $\alpha$-silyl-$\omega$-amino anchor stepwise by a solid phase peptide synthesis method with one or more $\alpha$-carboxyl-$\omega$-amino linker molecules and then in order from the C-terminal to the N-terminal of the peptide with each corresponding amino acid or amino acid-like compound and then finally with the N-terminal fluorescent marker molecule, using N-terminal protection and deprotection of each $\alpha$-carboxyl-$\omega$-amino linker molecule or amino acid or amino acid-like compound and protection and deprotection of any other functional group as needed.

In a second process aspect the invention is a biochemical assay method which comprises reacting in aqueous medium a protease and a substrate peptide or peptide having an amino acid-like moiety in place of an amino acid moiety thereof immobilized on glass beads by a C-terminal linker-anchor and marked by an N-terminal fluorescent marker, separating the resulting glass beads from the supernatant liquid, measuring the fluorescence of the supernatant liquid, and determining from the measured fluorescence the extent of cleavage of the substrate by the protease. By an additional step the site of cleavage of the substrate by the protease can be determined by sequential amino acid analysis.

By identifying substrates which undergo maximum cleavage by proteases the invention is useful in designing inhibitors of the proteases for use as drugs for diseases and disorders in which the proteases are involved.

DETAILED DESCRIPTION ON OF THE INVENTION

In the composition of matter aspect of the invention the peptide or peptide having an amino acid-like moiety in place of an amino acid moiety thereof can be of any length but preferably has from two to twenty amino acid or amino acid-like moieties. The amino acid can be any L- or D-amino acid or mixture thereof. The amino acid-like moiety is one which takes the place of one or more amino acid moieties in the peptide chain. More particularly it can be any of the twenty essential α-amino acids or a substituted derivative or analog thereof, for example sarcosyl or α-aminobutyryl, a β- or γ-amino acid moiety, for example γ-aminobutyryl, a moiety having a ring fusion within a single α-amino acid moiety, for example the moiety having the structural formula

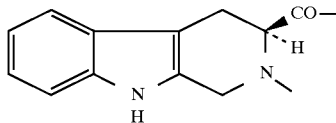

described by Singh et al. U.S. Pat. No. 4,839,465 and abbreviated therein as Tpi, which is tryptophyl fused between the α-amino and the 2-position of the indole ring by methylene, or a moiety having a ring fusion between two α-amino acid moieties, for example the moiety having the structural formula

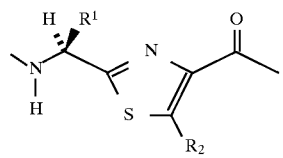

wherein $R_1$ is $CH_2$-3-indolyl and $R_2$ is Ph described by Gordon et al. (Eleventh American Peptide Symposium, San Diego, Calif., Jul. 9–14, 1989) as "the 'D-Trp-Phe' thiazole", that is, the tryptophylphenylalanyl moiety fused into a thiazole ring wherein a sulfur atom bridges the carbonyl carbon atom of tryptophyl and the β-carbon atom of phenylalanyl.

The glass of the glass bead is an inorganic oxide glass and can be a silicate, aluminosilicate, borosilicate or phosphosilicate glass or mixture thereof and is preferably porous and preferably has a density greater than that of the medium in which it is used. Controlled-pore glass is most preferable. The mean pore diameter is in the range of 50–5000 Ångstroms, preferably 170–1400 Ångstroms, most preferably 500–600 Ångstroms. The glass bead has a particle size in the range of 20–200 microns, preferably 37–125 microns, most preferably 37–74 microns (200/400 mesh).

In the first process aspect of the invention and the following description "corresponding" means that a variable in one structural formula has the same meaning in a different structural formula.

The anchor is an α-silyl-ω-amino moiety joined at the amino end to the C-terminal carboxyl carbon atom of the linker by an amide functional group and at the silyl end to the glass by a silyloxy functional group. Any moiety which does not interfere with formation of the two functional groups or with any of the peptide forming steps can separate the two functional groups. A preferred anchor has the structural formula

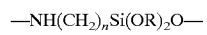  Formula Ia and the corresponding anchor molecule has the structural formula

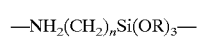  Formula Ib wherein n is an integer from 2 through 20 and R is hydrogen, methyl, ethyl or the glass bead. The anchor of Formula Ia wherein n is 3 and R is hydrogen is particularly preferred. The anchor can also have the structural formula

  Formula Ic and the corresponding anchor molecule has the structural formula

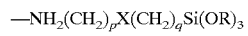  Formula Id wherein p and q are each an integer from 2 through 10, X is O, S, SO, $SO_2$ or NR and R is hydrogen, methyl, ethyl or the glass bead.

The linker is an α-carboxyl-ω-amino moiety joined at the amino end to the C-terminal carboxyl carbon atom of the peptide or peptide having an amino acid-like moiety in place of an amino acid moiety thereof by an amide functional group and at the carboxyl end to the amino nitrogen atom of the anchor by an amide functional group. Any moiety which does not interfere with formation of the two functional groups by the solid phase peptide forming steps whereby they are formed can separate the two functional groups. A preferred linker has the structural formula

  Formula IIa and the corresponding linker molecule has the structural formula

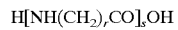  Formula IIb wherein r is an integer from 3 through 7 and is preferably 5 and s is an integer from 1 through 10. The linker can also have the structural formula

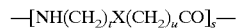  Formula IIc and the corresponding linker molecule has the structural formula

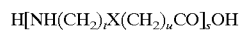  Formula IId wherein s is an integer from 1 through 10, t is an integer from 2 through 5, u is an integer from 1 through 4, X is O, S, SO, $SO_2$ or NR and R is hydrogen, methyl or ethyl. The linker molecules of Formula IIb or IId wherein s is 1 are generally known or can be prepared by known methods. The preferred compound of Formula IIb wherein r is 5 and s is 1 is 6-aminohexanoic acid (ε-aminocaproic acid, Acp). The linker of Formula IIa or IIc wherein s is greater than 1 is preferably formed in place by successive solid phase peptide forming steps.

The N-terminal fluorescent marker can be any fluorescent moiety bondable to the primary or secondary N-terminal amino nitrogen atom of the peptide or peptide having an amino acid-like moiety in place of an amino acid moiety thereof and is preferably bonded thereto by an amide or urethane linkage formed by reaction of the corresponding N-terminal fluorescent marker molecule and the peptide by a solid phase peptide synthesis method. The fluorescent marker molecules are generally known or can be prepared by known methods or by methods described herein. Examples of fluorescent markers which can be used are (9-fluorenyl)methoxycarbonyl, 2-(9-fluorenyl)acetyl, 2-aminobenzoyl ammonium salt, 2-(7-hydroxy-4-coumarinyl)acetyl and 3-(7-hydroxy-4-coumarinyl)propionyl of which 3-(7-hydroxy-4-coumarinyl)propionyl is particularly preferred and whose corresponding fluorescent marker molecules are the corresponding carboxylic acids.

Glass beads having the anchor already bonded thereto are commercially available and can be used directly for linker formation and peptide synthesis including the preferred controlled-pore glass beads having the anchor of Formula Ia wherein n is 3 and R is hydrogen or the glass bead and the controlled-pore glass beads having the anchor of Formula Ic wherein p and q are each 6, X is NH and R is hydrogen or the glass bead. Otherwise the reaction of the glass bead and the anchor molecule of Formula Ib or Id wherein R is methyl or ethyl is carried out with or without an inert solvent at a temperature in the range from 0° C. to 100° C. followed by removal of solvent if used and by-product methanol or ethanol. The anchor of Formula Ia or Ic wherein R is methyl or ethyl is hydrolyzed to the corresponding anchor of Formula Ia or Ic wherein R is hydrogen upon contact with water.

The protection, activation, condensation and deprotection steps of the solid phase peptide synthesis methods of the invention are carried out using the methods generally described by John Jones, "The Chemical Synthesis of Peptides" (Clarendon Press, Oxford, 1991).

Useful carboxyl-activated derivatives of the amino acids, amino acid-like compounds, linker molecules and fluorescent marker molecules of the invention are the acyl halides and pseudohalides including the acyl azides, the anhydrides including the symmetrical anhydrides and the mixed anhydrides including the mixed anhydrides with diphenylphosphinyl chloride or isobutyl chloroformate, derivatives formed by addition reactions including those using dicyclohexylcarbodiimide or diisopropylcarbodiimide, displaceable acyl derivatives of heterocyclic nitrogen, ring-openable activated heterocyclic systems, acylphosphonium derivatives, and activated esters including 1-hydroxybenzotriazole, N-hydroxysuccinimide and pentafluorophenyl esters. Carboxyl activation using diisopropylcarbodiimide and 1-hydroxybenzotriazole is preferred.

The N-terminal amino of the amino acid and any reactive side chain functional group thereof or of the peptide already immobilized on the glass bead must be protected as the new amide bond is formed. The preferred N-terminal amino protecting group is 9-fluorenylmethoxycarbonyl (Fmoc), which can be removed in the presence of t-butyloxycarbonyl under basic conditions, for example piperidine in dimethylformamide. The preferred side chain protecting groups are t-butyl for aspartyl, glutamyl, seryl, threonyl and tyrosyl, t-butyloxycarbonyl (Boc) for lysyl, trityl for histidyl, and 2,2,5,7,8-pentamethylchroman-6-sulfonyl (Pmc) for arginyl, which can be removed by acidic cleavage, for example, with trifluoroacetic acid, preferably trifluoroacetic acid containing water (about 5%) and a small amount each of ethanedithiol and thioanisole.

In solid phase peptide synthesis the C-terminal carboxyl of the immobilized amino acid or peptide is protected as an amide as the synthesis proceeds.

The solid phase synthetic methods of the invention are preferably carried out using an automated peptide synthesizer, controlled-pore silicate glass beads having a mean pore diameter of 500–600 Ångströms, particle size of 200/400 mesh, the anchor of Formula Ia wherein n is 3 and R is hydrogen, the linker of Formula IIa wherein r is 5, 3-(7-hydroxy-4-coumarinyl)propionyl as the N-terminal fluorescent marker, carboxyl activation using diisopropylcarbodiimide and 1-hydroxybenzotriazole, and 9-fluorenylmethoxycarbonyl (Fmoc) as the N-terminal protecting group. The preferred solvent for the linker forming steps is dimethylformamide. The preferred solvent for the peptide forming steps is N-methylpyrrolidinone.

In carrying out the peptide synthesis the structure of the peptide product is inferred from known structures of starting materials and expected courses of preparative reactions and is confirmed by amino acid analysis.

In carrying out the biochemical assay method of the invention the protease can be any protease whose ability to cleave the glass bead-linked peptide is desired to be tested, for example collagenase, thermolysin or stromelysin.

EXAMPLE

Anchor—Glass Bead

Controlled-pore silicate glass beads having a mean pore diameter of 585 Ångströms, particle size of 200/400 mesh, the anchor of Formula Ia wherein n is 3 and R is hydrogen and capacity of 0.077 milliequivalent/gram were purchased from CPG Inc., 32 Pier Lane West, Fairfield, N.J. 07004 under the name of Aminopropyl-CPG or AMP-CPG.

Preparation of 3-(7-Hydroxy-4-coumarinyl)propionic Acid as Marker Molecule

Succinic acid monoethyl ester mono acid chloride (90.53 g) was added dropwise with stirring at 0° C. to a solution of malonic acid cyclic isopropylidene ester (Meldrum's acid, 75.85 g) and pyridine (83.11 g) in dichloromethane (600 mL). Stirring was continued for one hour at 0° C. then for one hour at room temperature. The mixture was washed twice with hydrochloric acid (1.67M, 600 mL), dried over magnesium sulfate and stripped of volatiles. A solution of the residue in absolute ethanol (500 mL) was heated under reflux for two hours, let stand overnight and stripped of volatiles. The residue was distilled under vacuum (0.4 mm of mercury) affording 3-oxohexane-1,6-dioic acid diethyl ester in two fractions (8.9 g, b.r. 90°–104° C.; 88 g, b.p. 104° C.; total yield 85%).

A solution of 3-oxohexane-1,6-dioic acid diethyl ester (78.88 g), resorcinol (40.19 g) and ethanol (1 L) was saturated with hydrogen chloride gas during two hours at 0° C., tightly stoppered, let stand at room temperature over the weekend, shown by thin layer chromatography to contain unreacted 3-oxohexane-1,6-dioic acid diethyl ester, saturated again with hydrogen chloride gas during 45 minutes at 0° C., and let stand overnight at room temperature. Although thin layer chromatography still showed that the reaction was incomplete, the solution was partially (800 mL) stripped of volatiles and poured into ice-water. The resulting solid was collected by filtration and ethanol (300 mL) and aqueous sodium hydroxide solution (2.5N, 350 mL) were added. The mixture was stirred at room temperature and, when the reaction was complete, poured into hydrochloric acid (2N, 500 mL). A suspension of the resulting solid in methanol (300 mL) was stirred for 15 minutes at room temperature, cooled on ice and filtered. The resulting solid was washed with ether and dried affording 3-(7-hydroxy-4-coumarinyl) propionic acid (62.4 g, 73% yield).

Marker-Peptide-Linker-Anchor-Glass Bead Formation

An automated peptide synthesizer Model 350 MPS purchased from Advanced ChemTech Inc., P.O. Box 1403, Louisville, Ky. 40201 having a 96-tube capacity was used for the linker-, peptide- and marker-forming steps. A one-hundred milligram quantity of glass beads was weighed into each tube. Solvents and solutions were transferred into the tubes by injection and removed by aspiration. After injection and before aspiration the tubes were agitated by orbital shaking resulting in vortex-like mixing of the contents. All steps were carried at room temperature and humidity.

$\epsilon$-Aminocaproic acid was used as the linker molecule for forming the linker of Formula IIa wherein r is 5, which is represented as $(Acp)_5$. 3-(7-Hydroxy-4-coumarinyl) propionic acid was used as the marker molecule for forming as the N-terminal fluorescent marker 3-(7-hydroxy-4-coumarinyl)propionyl (Hcp). The following amino acids each identified by name and corresponding three-letter code were used to form a set of eight immobilized hexapeptides, one having the linker $(Acp)_s$ wherein s is each of the integers from 1 to 10 and the other seven each having the linker $(Acp)_7$, and one immobilized heptapeptide having the linker $(Acp)_7$:

|  |  |
|---|---|
| glycine | Gly |
| alanine | Ala |
| D-alanine | ala |
| leucine | Leu |
| phenylalanine | Phe |
| methionine | Met |
| proline | Pro |
| tryptophan | Trp |

The N-terminal protecting group for the amino acids and the $\epsilon$-aminocaproic acid was 9-fluorenylmethoxycarbonyl (Fmoc). None of the above-listed amino acids has a functional group in the side chain which required protection.

Preparatory to linker and peptide formation the glass beads in each tube were washed with dimethylformamide (500 $\mu$L) for one minute. A solution of the protected $\epsilon$-aminocaproic acid (amount calculated so that 500 $\mu$L of the solution would provide a tenfold excess thereof based on capacity of the glass beads), 1-hydroxybenzotriazole (10–20% excess based on protected $\epsilon$-aminocaproic acid) and diisopropylcarbodiimide (20–40% excess based on protected $\epsilon$-aminocaproic acid) in N-methylpyrrolidinone was allowed to stand for one hour prior to coupling to ensure complete formation of the activated ester. Coupling was carried out for 30 minutes with the resulting solution (500 $\mu$L) and was repeated to ensure complete reaction. Two solutions were prepared for each of the amino acid couplings and the 3-(7-hydroxy-4-coumarinyl)propionic acid couplings, one a solution of the protected amino acid or 3-(7-hydroxy-4-coumarinyl)propionic acid (amount calculated so that 350 $\mu$L of the solution would provide a tenfold excess thereof based on capacity of the glass beads) and 1-hydroxybenzotriazole (10–20% excess based on the protected amino acid or 3-(7-hydroxy-4-coumarinyl)propionic acid) in N-methylpyrrolidinone and the other a solution of diisopropylcarbodiimide (amount calculated so that 150 $\mu$L of the solution would provide a 20–40% excess thereof based on the protected amino acid or 3-(7-hydroxy-4coumarinyl)propionic acid) in N-methylpyrrolidinone. Coupling was carried out for 30 minutes with the resulting solution of protected amino acid and 1-hydroxybenzotriazole or 3-(7-hydroxy-4-coumarinyl) propionic acid and 1-hydroxybenzotriazole (350 $\mu$L) and the resulting diisopropylcarbodiimide solution (150 $\mu$L) and was repeated to ensure complete reaction. After each amino acid coupling step deprotection was carried out for one minute with dimethylformamide-piperidine (1:1, 500 $\mu$L), then for twelve minutes with dimethylformamide-piperidine (1:1, 500 $\mu$L), then with dimethylformamide alone eight times (one minute and 500 $\mu$L each time) to ensure complete removal of piperidine. After the 3-(7-hydroxy-4-coumarinyl)propionic acid coupling step deprotection was again carned out to remove any possible self-acylated 3-(7-hydroxy-4-coumarinyl)propionic acid, then final washes were carried out first with dimethylformamide (five times, one minute and 500 $\mu$L each time), then with methanol-dichloromethane (1:1, five times, one minute and 500 $\mu$L each time) and finally with dichloromethane (five times, one minute and 500 $\mu$L each time).

Marker-peptide-linker-anchor-glass bead products of the following formulas wherein R is hydrogen or the glass bead were thus prepared:

| Formula | Marker-Peptide-Linker-Anchor-Glass Bead Product | SEQ ID NO. |
|---|---|---|
| IIIa | Hcp-GlyProLeuAlaMetPhe-$(Acp)_1$-$NH(CH_2)_3Si(OR)_2$O-Glass Bead | 1 |
| IIIb | Hcp-GlyProLeuAlaMetPhe-$(Acp)_2$-$NH(CH_2)_3Si(OR)_2$O-Glass Bead | 1 |
| IIIc | Hcp-GlyProLeuAlaMetPhe-$(Acp)_3$-$NH(CH_2)_3Si(OR)_2$O-Glass Bead | 1 |
| IIId | Hcp-GlyProLeuAlaMetPhe-$(Acp)_4$-$NH(CH_2)_3Si(OR)_2$O-Glass Bead | 1 |
| IIIe | Hcp-GlyProLeuAlaMetPhe-$(Acp)_5$-$NH(CH_2)_3Si(OR)_2$O-Glass Bead | 1 |
| IIIf | Hcp-GlyProLeuAlaMetPhe-$(Acp)_6$-$NH(CH_2)_3Si(OR)_2$O-Glass Bead | 1 |
| IIIg | Hcp-GlyProLeuAlaMetPhe-$(Acp)_7$-$NH(CH_2)_3Si(OR)_2$O-Glass Bead | 1 |
| IIIh | Hcp-GlyProLeuAlaMetPhe-$(Acp)_8$-$NH(CH_2)_3Si(OR)_2$O-Glass Bead | 1 |
| IIIi | Hcp-GlyProLeuAlaMetPhe-$(Acp)_9$-$NH(CH_2)_3Si(OR)_2$O-Glass Bead | 1 |
| IIIj | Hcp-GlyProLeuAlaMetPhe-$(Acp)_{10}$-$NH(CH_2)_3Si(OR)_2$O-Glass Bead | 1 |

-continued

| Formula | Marker-Peptide-Linker-Anchor-Glass Bead Product | SEQ ID NO. |
|---------|------------------------------------------------|------------|
| IIIk | Hcp-AlaProLeuAlaLeuPhe-$(Acp)_7$-$NH(CH_2)_3Si(OR)_2$O-Glass Bead | 2 |
| IIIl | Hcp-GlyAlaLeuAlaLeuPhe-$(Acp)_7$-$NH(CH_2)_3Si(OR)_2$O-Glass Bead | 3 |
| IIIm | Hcp-GlyProAlaAlaLeuPhe-$(Acp)_7$-$NH(CH_2)_3Si$ $(OR)_2$O-Glass Bead | 4 |
| IIIn | Hcp-GlyProLeuAlaLeuPhe-$(Acp)_7$-$NH(CH_2)_3Si(OR)_2$O-Glass Bead | 5 |
| IIIo | Hcp-GlyProLeuAlaAlaPhe-$(Acp)_7$-$NH(CH_2)_3Si(OR)_2$O-Glass Bead | 6 |
| IIIp | Hcp-GlyProLeuAlaLeuAla-$(Acp)_7$-$NH(CH_2)_3Si(OR)_2$O-Glass Bead | 7 |
| IIIq | Hcp-AlaAlaAlaLeuTrpAlaAla-$(Acp)_7$-$NH(CH_2)_3Si(OR)_2$O-Glass Bead | 8 |
| IIIr | Hcp-$(ala)_6$-$(Acp)_7$-$NH(CH_2)_3Si(OR)_2$O-Glass Bead | 9 |

The immobilized peptides of formulas IIIe and IIIg were subjected to amino acid analysis with the following results:

| Product of | Amino Acid Relative Ratios | | | | | | |
|------------|------|------|------|------|------|------|------|
| Formula | Pro | Gly | Ala | Met | Leu | Phe | Acp |
| IIIe | 0.99 | 1.02 | 1.01 | 0.87 | 1.00 | 0.96 | 4.77 |
| IIIg | 0.97 | 1.03 | 1.01 | 0.85 | 1.00 | 0.96 | 7.18 |

Bioassay

The protease used was recombinant truncated collagenase of molecular weight 19,000, which was stored at 4° C. as a 10 μM stock aqueous solution and diluted to 30 nM just prior to carrying out the assay with aqueous buffer solution containing tromethamine (TRIS, 50 mM), sodium chloride solution (0.2M), calcium chloride (10 mM), and octoxynol-9 to 10 (Triton X-100, 0.1% v/v), whose pH was adjusted to 7.5 with aqueous sodium hydroxide solution and which was filtered and stored at 4° C. A 2- to 3-mg sample of the immobilized peptide was weighed into a 1.5-mL polypropylene microfuge tube. Sufficient buffer solution was added with vortexing to wet the immobilized peptide and make the concentration thereof 7.5 mg/mL. Sufficient collagenase solution was added to make the concentration thereof 10 nM, the tube was vortexed mechanically for 30–60 minutes, and the reaction was stopped by centrifuging. Part of the supernatant solution (200 μL) was transferred to a well of a 96-well plate. Fluorescence was measured at an excitation wavelength of 355 nm and an emission wavelength of 460 nm. The following mean fluorescence values from two measurements were obtained from the immobilized peptides of Formulas IIIa–r.

| Immobilized Peptide of Formula | Mean Fluorescence Value ± Deviation |
|---|---|
| IIIa | 2042.5 ± 13 |
| IIIb | 3824.5 ± 9 |
| IIIc | 5733.5 ± 132 |
| IIId | 6157.0 ± 72 |
| IIIe | 5838.5 ± 170 |
| IIIf | 7559.5 ± 2551 |
| IIIg | 5374.5 ± 53 |
| IIIh | 4723.5 ± 213 |
| IIIi | 4238.5 ± 192 |
| IIIj | 3662.5 ± 23 |
| IIIk | 3316.0 ± 57 |
| IIIl | 707.9 ± 266 |
| IIIm | 4283.0 ± 150 |
| IIIn | 2964.5 ± 136 |
| IIIo | 328.1 ± 0 |
| IIIp | 1913.5 ± 63 |
| IIIq | 379.5 ± 115 |
| IIIr | 201.8 ± 145 |

These fluorescence values show that the immobilized peptides of Formulas IIIa–IIIj wherein the linker varied from $(Acp)_1$ through $(Acp)_{10}$ underwent cleavage whose extent varied with the length of the linker, increasing from $(Acp)_1$ through $(Acp)_6$ and decreasing from $(Acp)_6$ through $(Acp)_{10}$, and that, of the various immobilized peptides having the linker $(Acp)_7$, which are those of Formulas IIIg and IIIk–r, the immobilized peptide of Formula IIIg underwent cleavage to the greatest extent. Fluorescence values can be converted to concentration values by comparison with a standard curve constructed using known concentrations of Hcp-GlyProLeuAla-OH (0–100 μM).

The site of cleavage of the immobilized peptide by the enzyme can be determined by analyzing by known methods the amino acid sequence of the peptide fragment in the supernatant solution or preferably the peptide fragment remaining immobilized on the glass beads.

What is claimed is:

1. A peptide immobilized on an aminopropyl controlled-pore silicate glass bead by a C-terminal linker having the formula $$-[NH(CH_2)_5CO]_s-$$

wherein s is an integer from 1 through 10, or a C-terminal linker having the formula $$-[NH(CH_2)_tX(CH_2)_uCO]_s-$$

wherein s is an integer from 1 through 10, t is an integer from 2 through 5, u is an integer from 1 through 4, X is O, S, SO, $SO_2$ or NR and R is hydrogen, methyl or ethyl and marked by an N-terminal fluorescent group bonded to the primary or secondary N-terminal amino nitrogen atom of the peptide.

2. An immobilized peptide according to claim 1 having the formula

```
Hep—Gly—Pro—Leu—Ala—Met—Phe—(Acp)2AMP—CPG (SEQ ID NO. 1)
 1                   5
```

3. Aminopropyl controlled-pore silicate glass beads bearing peptides bonded thereto via a C-terminal linker according to claim 1, wherein each peptide is marked by an N-terminal fluorescent group bonded to the primary or secondary N-terminal amino nitrogen atom of the peptide.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( D ) TOPOLOGY: linear (i i) MOLECULE TYPE: peptide (i x) SEQUENCE DESCRIPTION: SEQ ID NO: 1:

Gly Pro Leu Ala Met Phe
1               5

(2) INFORMATION FOR SEQ ID NO:2:

(i) SEQUENCE CHARACTERISTICS:
        (A) LENGTH: 6 amino acids
        (B) TYPE: amino acid
        (D) TOPOLOGY: linear (i i) MOLECULE TYPE: peptide (i x) SEQUENCE DESCRIPTION: SEQ ID NO: 2:

Ala Pro Leu Ala Leu Phe
1               5

(2) INFORMATION FOR SEQ ID NO:3:

(i) SEQUENCE CHARACTERISTICS:
        (A) LENGTH: 6 amino acids
        (B) TYPE: amino acid
        (D) TOPOLOGY: linear (i i) MOLECULE TYPE: peptide (i x) SEQUENCE DESCRIPTION: SEQ ID NO: 3:

Gly Ala Leu Ala Leu Phe
1               5

(2) INFORMATION FOR SEQ ID NO:4:

(i) SEQUENCE CHARACTERISTICS:
        (A) LENGTH: 6 amino acids
        (B) TYPE: amino acid
        (D) TOPOLOGY: linear (i i) MOLECULE TYPE: peptide (i x) SEQUENCE DESCRIPTION: SEQ ID NO: 4:

Gly Pro Ala Ala Leu Phe
1               5

(2) INFORMATION FOR SEQ ID NO:5:

(i) SEQUENCE CHARACTERISTICS:
        (A) LENGTH: 6 amino acids
        (B) TYPE: amino acid
        (D) TOPOLOGY: linear (i i) MOLECULE TYPE: peptide (i x) SEQUENCE DESCRIPTION: SEQ ID NO: 5:

Gly Pro Leu Ala Leu Phe
1               5

(2) INFORMATION FOR SEQ ID NO:6:

(i) SEQUENCE CHARACTERISTICS:
        (A) LENGTH: 6 amino acids
        (B) TYPE: amino acid
        (D) TOPOLOGY: linear (i i) MOLECULE TYPE: peptide (i x) SEQUENCE DESCRIPTION: SEQ ID NO: 6:

Gly Pro Leu Ala Ala Phe (2) INFORMATION FOR SEQ ID NO:7:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) SEQUENCE DESCRIPTION: SEQ ID NO: 7:

```
Gly  Pro  Leu  Ala  Leu  Ala
1                   5
```

(2) INFORMATION FOR SEQ ID NO:8:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (ix) SEQUENCE DESCRIPTION: SEQ ID NO: 8:

```
Ala  Ala  Ala  Leu  Trp  Ala  Ala
1                   5
```

(2) INFORMATION FOR SEQ ID NO:9:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) SEQUENCE DESCRIPTION: SEQ ID NO: 9:

```
Xaa  Xaa  Xaa  Xaa  Xaa  Xaa
1                   5
```